United States Patent
Isota et al.

[11] Patent Number: 6,118,029
[45] Date of Patent: Sep. 12, 2000

[54] PROCESS FOR PRODUCING 3,3',5,5'-TETRA-T BUTYLBIPHENOL

[75] Inventors: Yoichiro Isota; Kazuhiko Yao; Mikio Kawahara, all of Wakayama, Japan

[73] Assignee: Honshu Chemical Industry Co., Ltd., Tokyo, Japan

[21] Appl. No.: 09/015,962

[22] Filed: Jan. 30, 1998

[30] Foreign Application Priority Data

Jan. 30, 1997 [JP] Japan .................................. 9-016895
Jan. 30, 1997 [JP] Japan .................................. 9-016896

[51] Int. Cl.[7] .................................................. C07C 39/12
[52] U.S. Cl. ........................... 568/730; 568/722; 568/803
[58] Field of Search ............................. 568/722, 730, 568/803

[56] References Cited

U.S. PATENT DOCUMENTS

| | | | |
|---|---|---|---|
| 3,493,511 | 2/1970 | Law | 568/730 |
| 4,487,977 | 12/1984 | Kruse et al. | 568/730 |
| 4,847,434 | 7/1989 | Mina et al. | 568/930 |
| 4,891,453 | 1/1990 | Tanaka et al. | 568/805 |
| 5,099,076 | 3/1992 | Takahashi et al. | 568/730 |
| 5,324,868 | 6/1994 | Inaba et al. | 568/805 |

FOREIGN PATENT DOCUMENTS

| | | |
|---|---|---|
| 0011296A1 | 5/1982 | European Pat. Off. . |
| 0309226A2 | 3/1989 | European Pat. Off. . |
| 0421883A2 | 4/1991 | European Pat. Off. . |
| A3123747 | 5/1991 | Japan . |
| 597740 | 4/1993 | Japan . |

OTHER PUBLICATIONS

Database WPI, Section Ch, Week 9320, Derwent Publications Ltd., London, GB; Class A41, An 93–164392, XP002064633, & JP 05 097 740 A (Mitsubishi Petrochemical Co., Ltd.); (Apr. 20, 1993) Abstract.

Database WPI, Section Ch, Week 8642, Derwent Publications Ltd., London, GB; Class A41, AN 86–275562, XP002064634 & JP 61 200 935 A (Honshu Kagaku Kogyo KK) (Sep. 5, 1986) Abstract.

*Primary Examiner*—James O. Wilson
*Attorney, Agent, or Firm*—Birch, Stewart, Kolasch & Birch, LLP

[57] ABSTRACT

A batch or continuous process produces highly pure 3,3',5,5'-tetra-t-butylbiphenol suitable as a starting material for the synthesis of 4,4'-biphenol. The process for producing 3,3',5,5'-tetra-t-butylbiphenol comprises conducting an oxidation coupling of purified 2,6-di-t-butylphenol(i) or crude 2,6-di-t-butylbiphenol(ii), said crude 2,6-di-t-butylphenol being obtained by reacting isobutylene with phenol in the presence of an aluminum catalyst, and removing the aluminum catalyst. The 2,6-di-t-butylphenol is oxidatively coupled in an alkali metal catalyst mixture comprising (1) an alkali metal catalyst and alkylphenols, or (2) alkali metal catalyst, alkylphenols and phenol to produce 3,3',5,5'-tetra-t-butylbiphenol. The oxidative coupling is conducted together with 10–30% by weight of phenol and/or t-butylphenol per 100% by weight of 2,6-di-t-butylphenol in the presence of an alkali metal catalyst.

16 Claims, No Drawings

PROCESS FOR PRODUCING 3,3',5,5'-TETRA-T BUTYLBIPHENOL

FIELD OF THE INVENTION

The present invention relates to a process for producing 3,3',5,5'-tetra-t-butylbiphenol. More particularly, the present invention is concerned with a process for producing 3,3',5,5'-tetra-t-butylbiphenol useful as a starting material of, for example, 4,4'-biphenol through an oxidative coupling of purified 2,6-di-t-butylphenol or crude 2,6-di-t-butylphenol. Further, the present invention is concerned with a process for producing 3,3',5,5'-tetra-t-butylbiphenol suitably employed as a starting material of a 4,4'-biphenol of high quality which is highly purified and is free from coloration.

BACKGROUND OF THE INVENTION

It is common practice to use an alkali metal hydroxide such as sodium hydroxide or potassium hydroxide as a catalyst in the oxidative coupling of 2,6-di-t-butylphenol.

Japanese Patent Laid-open Publication No. 5(1993)-97740 discloses that the above alkali metal hydroxide can be used not only in the form of a solution but also in anhydrous or nonsolvent form.

However, when the alkali metal catalyst such as an alkali metal hydroxide is dissolved in water to thereby obtain an aqueous solution (e.g., 48% aqueous KOH solution) and used as the catalyst as mentioned above, the alkali metal catalyst falls in the form of solution drops to the bottom of the reaction vessel because the solubility of alkali metal catalyst in 2,6-di-t-butylphenol is low. Thereafter, water vaporization occurs, so that the alkali metal catalyst cannot be homogeneously dispersed in the 2,6-di-t-butylphenol placed in the reaction vessel.

Therefore, problems have been encountered such that the oxidative coupling reaction rate is decreased and the amount of impurities is increased to thereby lower the yield of 3,3',5,5'-tetra-t-butylbiphenol and cause an aeration port of the reaction vessel to have an increased likelihood to clog up.

The occurrence of the above heterogeneous dispersion of alkali metal catalyst in the reaction system disenables the continuous oxidation reaction.

A large amount of alkali metal catalyst must be used for preventing the lowering of oxidative coupling reaction rate. However, at that time, it is also necessary to add a large amount of acid compound for neutralization.

With respect to the purified 2,6-di-t-butylphenol, the phenol content thereof is generally not greater than 0.1% by weight and, thus, it substantially does not contain phenol. Further, in the purified 2,6-di-t-butylphenol, the content of o-t-butylphenol is generally not greater than 0.1% by weight and the content of t-butylphenols other than o-t-butylphenol is generally not greater than 0.5% by weight.

In the oxidative coupling of the purified 2,6-di-t-butylphenol as a starting material of 3,3',5,5'-tetra-t-butylbiphenol in the presence of an alkali metal catalyst, an increase in the degree of oxidation of 2,6-di-t-butylphenol lowers the selectivity of desired 3,3',5,5'-tetra-t-butylbiphenol and increases the formation of by-products such as 3,3',5,5'-tetra-t-butyldiphenoquinone, 2,6-di-t-butylbenzoquinone and carbon dioxide contained in oxidation waste gas.

The above increase in the formation of by-products promotes the conversion of reaction products to a tar with the result that the color of the oxidation reaction mixture (3,3',5,5'-tetra-t-butylbiphenol containing by-products) deteriorates, and 3,3',5,5'-tetra-t-butylbiphenol is debutylated to thereby deteriorate the quality (purity and color) of obtained 4,4'-biphenol.

On the other hand, the crude 2,6-di-t-butylphenol obtained by reacting phenol with isobutylene in the presence of an aluminum phenoxide catalyst generally contains phenol, o-t-butylphenol, t-butylphenols other than o-t-butylphenol and 2,4,6-tri-t-butylphenol and 2,6-di-t-butylphenol in respective amounts of up to 1% by weight, up to 5% by weight, up to 3% by weight and 73 to 82% by weight of 2,6-di-t-butylphenol. When a large amount of starting material phenol and by-product o-t-butylphenol remain in the phenol butylating reaction mixture, the yield of 2,6-di-t-butylphenol decreases.

In the oxidative coupling of the crude 2,6-di-t-butylphenol as a starting material of 3,3',5,5'-tetra-t-butylbiphenol in the presence of an alkali metal catalyst, as in the oxidative coupling of purified 2,6-di-t-butylphenol, an increase in the degree of oxidation of 2,6-di-t-butylphenol lowers the selectivity of desired 3,3',5,5'-tetra-t-butylbiphenol and increases the formation of by-products such as 3,3',5,5'-tetra-t-butyldiphenoquinone, 2,6-di-t-butylbenzoquinone and carbon dioxide gas. Furthermore, the amount of products of oxidative coupling of 2,6-di-t-butylphenol with t-butylphenols mixed in the crude 2,6-di-t-butylphenol is increased.

Moreover, when 4,4'-biphenol is produced from 3,3',5,5'-tetra-t-butylbiphenol regardless if either the purified 2,6-di-t-butylphenol or the crude 2,6-di-t-butylphenol is used as the starting material of, trihydroyxbiphenyl occurs in the 3,3',5,5'-tetra-t-butylbiphenol debutylating reaction mixture. Additionally, an increase in the degree of oxidation of 2,6-di-t-butylphenol would increase the occurrence of trihydroxybiphenyl and invite deteriorations of the purity and color of 4,4'-biphenol.

Therefore, in the common oxidation, the oxidative coupling of 2,6-di-t-butylphenol must be conducted while restricting the degree of oxidation of 2,6-di-t-butylphenol at 75 to 85 mol % so that the formation of trihydroxybiphenyl in large amount can be prevented.

For obtaining the starting material of 3,3',5,5'-tetra-t-butylbiphenol which ensures production of high-quality 4,4'-biphenol while minimizing the formation of the above by-products, the degree of oxidation of 2,6-di-t-butylphenol must be held low while preventing the amount of 2,6-di-t-butylphenol in the oxidative reaction mixture from becoming smaller than a given level.

However, when the degree of oxidation of 2,6-di-t-butylphenol is held low, the problem is encountered that the 2,6-di-t-butylphenol charged in the reaction vessel cannot be satisfactorily utilized in the production of 3,3',5,5'-tetra-t-butylbiphenol from 2,6-di-t-butylphenol.

The inventors have made extensive and intensive studies with a view toward solving the above problems. As a result, it has been found that, in the catalytic oxidative coupling reaction of 2,6-di-t-butylphenol, the solubility of alkali metal catalyst in 2,6-di-t-butylphenol is markedly increased by the use of the alkali metal catalyst in combination with alkylphenols such as t-butylphenols or a liquid mixture of alkylphenols such as t-butylphenols and phenol, so that the oxidative reaction is homogeneously advanced to thereby enable producing 3,3',5,5'-tetra-t-butylbiphenol with high oxidation efficiency with the reduced occurrence of by-products such as carbon dioxide gas and 2,6-di-t-butylbenzoquinone. Moreover, it has been found that the oxidative coupling of purified 2,6-di-t-butylphenol or crude 2,6-di-t-butylphenol together with a given amount of phenol, o-t-butylphenol or other t-butylphenols in the presence of an alkali metal catalyst enables suppressing the formation of by-products such as 3,3',5,5'-tetra-t-butyldiphenoquinone, 2,6-di-t-butylbenzoquinone and carbon dioxide gas (impurities) even if the degree of oxidation of 2,6-di-t-butylphenol is increased to, for example, about 95%, and that the occurrence of trihydroxybiphenyl in the 3,3',5,5'-tetra-t-butylbiphenol debutylating reaction mixture can be inhibited in the production 4,4'-biphenol from the above 3,3',5,5'-tetra-t-butylbiphenol. The present invention has been completed on the basis of the above findings.

OBJECT OF THE INVENTION

The present invention has been made with a view toward solving the above problems of the prior art. Thus, it is an object of the present invention to provide a process for producing 3,3',5,5'-tetra-t-butylbiphenol in high yield through a homogeneous dispersion of an alkali metal catalyst, which process can be conducted in a continuous manner. It is another object of the present invention to provide a process for producing 3,3',5,5'-tetra-t-butylbiphenol from 2,6-di-t-butylphenol in high yield while fully utilizing the 2,6-di-t-butylphenol charged in the reaction vessel without detriment to the selectivity of 3,3',5,5'-tetra-t-butylbiphenol.

SUMMARY OF THE INVENTION

The first process for producing 3,3',5,5'-tetra-t-butylbiphenol according to the present invention comprises conducting an oxidative dimerization of purified 2,6-di-t-butylphenol (i) or crude 2,6-di-t-butylphenol (ii) obtained by reacting isobutylene with phenol in the presence of an aluminum catalyst and removing the aluminum catalyst, in the presence of an alkali metal catalyst to thereby obtain 3,3',5,5'-tetra-t-butylbiphenol, wherein a catalyst mixture (1) composed of an alkali metal catalyst and alkylphenols or a catalyst mixture (2) composed of an alkali metal catalyst, alkylphenols and phenol is used as the alkali metal catalyst for producing 3,3',5,5'-tetra-t-butylbiphenol.

It is preferred that the alkylphenols be contained in the catalyst mixture (1) or catalyst mixture (2) in an amount of 1 to 5 times mole of the alkali metal catalyst, and that water be contained in the catalyst mixture (1) or catalyst mixture (2) in an amount of 2 to 20% by weight. The catalyst mixture (2) preferably contains alkylphenols and phenol in a weight ratio of alkylphenols/phenol of at least 70/30.

The above catalyst mixture (1) and catalyst mixture (2) can instantaneously be dissolved in the 2,6-di-t-butylphenol reaction mixture. Therefore, the process for producing 3,3',5,5'-tetra-t-butylbiphenol according to the present invention enables continuously feeding the starting material and the catalyst and, hence, is most suitable for a continuous production of 3,3',5,5'-tetra-t-butylbiphenol.

The second process for producing 3,3',5,5'-tetra-t-butylbiphenol according to the present invention comprises conducting an oxidative coupling of purified 2,6-di-t-butylphenol (i) or crude 2,6-di-t-butylphenol (ii) obtained by reacting isobutylene with phenol in the presence of an aluminum catalyst and removing the aluminum catalyst, in the presence of an alkali metal catalyst to thereby obtain 3,3',5,5'-tetra-t-butylbiphenol, wherein the oxidative coupling is conducted in the presence of 10 to 30% by weight of phenol and/or t-butylphenols per 100% by weight of 2,6-di-t-butylphenol.

It is preferred that the t-butylphenols consist of o-t-butylphenol.

Further, it is preferred that the crude 2,6-di-t-butylphenol (ii) be obtained by reacting isobutylene with phenol in the presence of an aluminum phenoxide catalyst and contain phenol in an amount of not greater than 1.0% by weight, o-t-butylphenol in an amount of not greater than 5% by weight and t-butylphenols other than o-t-butylphenol and 2,4,6-tri-t-butylphenol in an amount of not greater than 3% by weight.

In the present invention, phenol together with an alkali metal catalyst may be added to purified 2,6-di-t-butylphenol or crude 2,6-di-t-butylphenol, or phenol may be directly added to purified 2,6-di-t-butylphenol or crude 2,6-di-t-butylphenol so that 10 to 30% by weight of phenol or 10 to 30% by weight of a total of phenol and o-t-butylphenol is present together with 100% by weight of 2,6-di-t-butylphenol. Also, t-butylphenols or t-butylphenols together with phenol may be directly added to purified 2,6-di-t-butylphenol or crude 2,6-di-t-butylphenol so that 10 to 30% by weight of t-butylphenols or 10 to 30% by weight of a total of t-butylphenols and phenol are present together with 100% by weight of 2,6-di-t-butylphenol.

DETAILED DESCRIPTION OF THE INVENTION

The process for producing 3,3',5,5'-tetra-t-butylbiphenol according to the present invention will be described in detail below.

Firstly, the first process for producing 3,3',5,5'-tetra-t-butylbiphenol according to the present invention will be illustrated.

The first process for producing 3,3',5,5'-tetra-t-butylbiphenol according to the present invention comprises conducting an oxidative dimerization of purified 2,6-di-t-butylphenol (i) or crude 2,6-di-t-butylphenol (ii) obtained by reacting isobutylene with phenol in the presence of an aluminum catalyst and removing the aluminum catalyst, in the presence of an alkali metal catalyst to thereby obtain 3,3',5,5'-tetra-t-butylbiphenol, wherein a catalyst mixture (1) composed of an alkali metal catalyst and alkylphenols or a catalyst mixture (2) composed of an alkali metal catalyst, alkylphenols and phenol is used as the alkali metal catalyst for producing 3,3',5,5'-tetra-t-butylbiphenol.

Starting Material

The starting material of 3,3',5,5'-tetra-t-butylbiphenol for use in the present invention is purified 2,6-di-t-butylphenol or crude 2,6-di-t-butylphenol.

The crude 2,6-di-t-butylphenol is, for example, a 2,6-di-t-butylphenol composition comprising 2,6-di-t-butylphenol and by-products, produced from phenol and isobutylene, as described in Japanese Patent Publication No. 6(1994)-74227.

In the process for producing p,p'-biphenol as described in Japanese Patent Publication No. 6(1994)74227, the content of 2,6-di-t-butylphenol and the content of phenol and p-t-butylphenol (PTBP) among byproducts in the crude 2,6-di-t-butylphenol (by-product containing 2,6-di-t-butylphenol composition mentioned above) are 73 to 82% by weight and up to 0.5% by weight, respectively.

Alkali Metal Catalyst

Examples of alkali metal catalysts suitably employed in the present invention include a hydroxide, a carbonate and a bicarbonate of an alkali metal. Of these, an alkali metal hydroxide is preferred.

The preferred form is a solution of the alkali metal hydroxide. Further, the alkali metal is preferably sodium and potassium, especially potassium.

Although the amount of added alkali metal catalyst is not particularly limited, it is generally preferred that the alkali metal catalyst be used in an amount ranging from 0.3 to 1.5 mol % per 100 mol % of charged 2,6-di-t-butylphenol from the viewpoint that too small an amount thereof causes the reaction rate to be low and too large an amount thereof requires a large quantity of acid for neutralization.

In the present invention, the alkali metal catalyst is used in the form of a catalyst mixture (1) comprising the alkali metal catalyst mixed with alkylphenols or in the form of a catalyst mixture (2) comprising the alkali metal catalyst mixed with a liquid mixture of alkylphenols and phenol.

Examples of alkylphenols suitably employed in the above catalyst mixtures (1) and (2) include t-butylphenols, cresols, xylenols, propylphenols, sec-butylphenols and mixtures thereof. Of these, t-butylphenols are preferred.

Specific examples of the t-butylphenols include o-t-butylphenol (OTBP), p-t-butylphenol (PTBP), m-t-butylphenol (MTBP), 2,4-di-t-butylphenol (2,4TBP) and mixtures thereof. Of these, p-t-butylphenol (PTBP) is preferred.

Although not particularly limited, the amount of alkylphenols (solvent) such as t-butylphenols added is preferably such that the concentration of the alkali metal catalyst ranges 5 to 15%. When the alkali concentration is too high, a mixture of the alkali metal catalyst and alkylphenols has a reduced tendency to be liquid at low temperatures. On the other hand, when the alkali concentration is too low, the alkylphenols for catalyst mixing are needed in greater amount, thereby increasing the formation of oxidative coupling by-products from the alkylphenols and 2,6-di-t-butylphenol. Further, it is preferred that the water content of each catalyst mixture be adjusted so as to fall within the range of 2 to 20% by weight. When the water content is too low, the freezing point of the catalyst mixture becomes high and the catalyst mixture has a reduced tendency to be liquid at low temperatures. On the other hand, when the water content is too high, the solubility of the catalyst mixture in 2,6-di-t-butylphenol is lowered with the result that the catalyst mixture is likely to settle in the form of liquid drops on the bottom of the reaction vessel.

The content of alkylphenols in each of the above catalyst mixtures (1) and (2) generally ranges from 1 to 5 mol and preferably from 2 to 4 mol per mol of the alkali metal catalyst. The water content of the catalyst mixture is in the range of 2 to 20% by weight, preferably, 5 to 15% by weight.

In the use of the above crude 2,6-di-t-butylphenol composition as a starting material of 3,3',5,5'-tetra-t-butylbiphenol, the amount of by-product alkylphenols such as o-t-butylphenol (OTBP), p-t-butylphenol (PTBP), 2,4-di-t-butylphenol (2,4TBP) and 2,4,6-tri-t-butylphenol (2,4,6TBP) is considered when the proportion of alkylphenols to be mixed with the alkali metal catalyst is determined.

In the present invention, a liquid mixture of the alkylphenols and phenol can be used in place of the alkylphenols in order to lower the freezing point of the catalyst mixture (1) composed of the alkali metal catalyst and alkylphenols. That is, the catalyst mixture (2) can be used in place of the catalyst mixture (1).

It is preferred that the above liquid mixture consist of p-alkylphenols and phenol, especially, p-t-butylphenol and phenol.

The weight ratio of alkylphenols to phenol [alkylphenols/phenol] in the above catalyst mixture (2) is preferably at least 70/30. When the proportion of phenol is too high, the situation is the same as in the use of an aqueous solution of alkali metal hydroxide alone and the catalyst mixture settles in the form of liquid drops on the bottom of the reaction vessel.

In the use of the above crude 2,6-dialkylphenol composition as a starting material of 3,3',5,5'-tetra-t-butylbiphenol, the respective amounts of by-product alkylphenols and phenol are considered when the proportions of alkylphenols and phenol to be mixed with the alkali metal catalyst are determined.

The method of mixing the alkali metal catalyst, alkylphenols and phenol is not particularly limited. Generally, the alkylphenols are mixed with phenol in a given ratio to thereby obtain a liquid mixture, and the alkali metal catalyst is added to the liquid mixture and mixed.

When the alkali metal catalyst is solid, a catalyst heating and dissolving operation is required. When the alkali metal catalyst is an aqueous solution of a hydroxide, the aqueous solution of alkali metal hydroxide is mixed with a liquid mixture of alkylphenols and phenol, optionally followed by heating and dehydration, and used in the catalytic reaction. Preferably, heating and dehydration are not conducted.

The alkali metals used as a catalyst, alkylphenols and liquid mixture of alkylphenols and phenol are soluble in arbitrary proportions in the purified 2,6-di-t-butylphenol, 2,6-di-t-butylphenol composition and oxidation reaction mixture thereof, so that they can be used in both a batch reaction and a continuous reaction.

That is, not only is it feasible to first add the purified 2,6-di-t-butylphenol or crude 2,6-di-t-butylphenol and the catalyst mixture (1) or (2), secondly heat the mixture to a given temperature and thirdly blow air or other oxygen containing gas thereinto to thereby carry out an oxidative reaction but also the purified 2,6-di-t-butylphenol or crude 2,6-di-t-butylphenol together with the catalyst mixture (1) or (2) can continuously be charged while performing an oxidative reaction.

The above catalyst mixture (1) or (2) and purified 2,6-di-t-butylphenol or crude 2,6-di-t-butylphenol can separately be introduced in the reaction vessel. Alternatively, the catalyst mixture (1) or (2) and purified 2,6-di-t-butylphenol or crude 2,6-di-t-butylphenol can be mixed together just prior to introduction into the reaction vessel, and thereby introduced into the reaction vessel.

The oxidative reaction temperature ranges from 150 to 250° C., preferably, from 180 to 200° C. Although the reaction pressure may be atmospheric or superatmospheric, the oxidative reaction is preferably conducted at 1 to 5 kg/cm².

Although the oxygen source for use in the oxidative reaction may be selected from among pure oxygen, air and an oxygen containing gas diluted with inert gas, the oxidative reaction is generally preferably conducted with the use of air or air diluted with nitrogen gas.

The amount of oxygen absorbed by the 2,6-di-t-butylphenol as a starting material of 3,3',5,5'-tetra-t-butylbiphenol ranges from 10 to 30 mol %, preferably, from 15 to 25 mol % per 100 mol % of charged 2,6-di-t-butylphenol.

When the oxygen absorption is low, 2,6-di-t-butylphenol remains unreacted in greater proportion to thereby lower the yield of 3,3',5,5'-tetra-t-butylbiphenol. On the other hand, when the oxygen absorption is too high, a large amount of by-products such as 3,3',5,5'-tetra-t-butyldiphenoquinone (DPQ) occur.

The above first process for producing 3,3',5,5'-tetra-t-butylbiphenol according to the present invention enables homogeneously performing the oxidative coupling reaction through a homogeneous dispersion of the alkali metal catalyst in the starting material with the result that 3,3',5,5'-tetra-t-butylbiphenol can be obtained in high yield.

The second process for producing 3,3',5,5'-tetra-t-butylbiphenol according to the present invention will now be described in detail.

In the common process for producing 3,3',5,5'-tetra-t-butylbiphenol which comprises conducting an oxidative coupling of 2,6-di-t-butylphenol in the presence of an alkali metal catalyst, the improvement of the second process for producing 3,3',5,5'-tetra-t-butylbiphenol according to the present invention comprises conducting the oxidative coupling in purified 2,6-di-t-butylphenol or crude 2,6-di-t-butylphenol in the presence of 10 to 30% by weight of phenol and/or t-butylphenols per 100% by weight of 2,6-di-t-butylphenol.

Starting Material

The starting material of 3,3',5,5'-tetra-t-butylbiphenol for use in the present invention is purified 2,6-di-t-butylphenol or crude 2,6-di-t-butylphenol.

In the purified 2,6-di-t-butylphenol, as mentioned above, the phenol content thereof is generally not greater than 0.1% by weight. Further, in the purified 2,6-di-t-butylphenol, the content of o-t-butylphenol is generally not greater than 0.1% by weight and the content of t-butylphenols other than o-t-butylphenol is generally not greater than 0.5% by weight.

The crude 2,6-di-t-butylphenol is, for example, a 2,6-di-t-butylphenol composition comprising 2,6-di-t-butylphenol and by-products, produced from phenol and isobutylene, as described in Japanese Patent Publication No. 6(1994)-74227.

In the process for producing p,p'-biphenol as described in Japanese Patent Publication No. 6(1994)-74227, generally, the content of phenol, the content of o-t-butylphenol (OTBP), the content of t-butylphenols other than o-t-butylphenol and 2,4,6-tri-t-butylphenol and the content of 2,6-di-t-butylphenol in the crude 2,6-di-t-butylphenol (by-product containing 2,6-di-t-butylphenol composition mentioned above) are up to 0.5% by weight, up to 5% by weight, up to 3% by weight and 73 to 82% by weight, respectively.

Alkali Metal Catalyst

Examples of alkali metal catalysts suitably employed in the present invention include alkali metal hydroxides such as sodium hydroxide and potassium hydroxide, alkali metal carbonates such as sodium carbonate and potassium carbonate, and alkali metal bicarbonates such as sodium hydrogen carbonate and potassium hydrogen carbonate. Of these, potassium hydroxide and potassium carbonate are preferred.

Although the amount of added alkali metal catalyst is not particularly limited, it is generally preferred that the alkali metal catalyst be used in an amount ranging from 0.3 to 1.5 mol % per 100 mol % of charged 2,6-di-t-butylphenol from the viewpoint that too small an amount thereof causes the reaction rate to be low and too large an amount thereof requires a large quantity of acid for neutralization.

Phenol and t-butylphenols

In the present invention, phenol may be added to purified 2,6-di-t-butylphenol or crude 2,6-di-t-butylphenol so that the phenol content of purified 2,6-di-t-butylphenol or crude 2,6-di-t-butylphenol is adjusted to range from 10 to 30% by weight, preferably, from 10 to 20% by weight and, still preferably, from 10 to 15% by weight.

Alternatively, t-butylphenols, preferably, o-t-butylphenol or o-t-butylphenol together with phenol may be added to purified 2,6-di-t-butylphenol or crude 2,6-di-t-butylphenol so that the content of t-butylphenols, preferably, the content of o-t-butylphenol or the total content of o-t-butylphenol and phenol in purified 2,6-di-t-butylphenol or crude 2,6-di-t-butylphenol is adjusted to range from 10 to 30% by weight, preferably, from 10 to 20% by weight and, still preferably, from 10 to 15% by weight.

The above amounts of added phenol and added t-butylphenols are determined, taking into account the amounts of phenol and t-butylphenols contained as by-products in purified 2,6-di-t-butylphenol and crude 2,6-di-t-butylphenol.

The above formation of by-products can be suppressed by, and the desired 3,3',5,5'-tetra-t-butylbiphenol can be efficiently produced by conducting the oxidative reaction of 2,6-di-t-butylphenol in the presence of the alkali metal catalyst while regulating the contents of phenol and t-butylphenols in purified 2,6-di-t-butylphenol so as to fall within the above ranges even if the degree of oxidation is high. This is also true in the use of crude 2,6-di-t-butylphenol.

Although the functions of phenol and t-butylphenols such as o-t-butylphenol have not yet been fully elucidated, it is presumed that the phenol and t-butylphenols act to not only homogeneously disperse the alkali metal catalyst in the 2,6-di-t-butylphenol reaction mixture but also capture reaction active substance associated with side reactions. The reasons for this presumption are that the effect of suppressing the above formation of by-products is slight when the amount of added phenol and t-butylphenols is too small, while the reaction rate is decreased when the above amount is too large and that, as long as the amount is suitable, the occurrence of carbon dioxide gas is decreased.

Examples of the t-butylphenols other than o-t-butylphenol and 2,4,6-tri-t-butylphenol include p-t-butylphenol (PTBP), m-t-butylphenol (MTBP), 2,4-di-t-butylphenol (2,4TBP) and mixtures thereof.

In the present invention, 10 to 30% by weight of phenol is caused to be present together with 100% by weight of 2,6-di-t-butylphenol by adding phenol together with the alkali metal catalyst to purified 2,6-di-t-butylphenol or crude 2,6-di-t-butylphenol or by directly adding phenol to purified 2,6-di-t-butylphenol or crude 2,6-di-t-butylphenol. The latter method of directly adding phenol is preferred. When added to the purified or crude 2,6-di-t-butylphenol which contains phenol in the above amount, the liquid mixture obtained by dissolving an alkali metal as an oxidizing catalyst in a liquid mixture of phenol and t-butylphenols is instantaneously homogeneously dissolved therein so that the oxidative coupling reaction is smoothly advanced.

When the alkali metal is dissolved in the liquid mixture of phenol and t-butylphenols, the amount of the liquid mixture is generally adjusted so as to be 1 to 10 times mole, preferably, 1 to 5 times mole per mole of the alkali metal catalyst.

With respect to the t-butylphenols or the liquid mixture of t-butylphenols and phenol, the t-butylphenols or the liquid mixture of t-butylphenols and phenol is directly added to purified 2,6-di-t-butylphenol or crude 2,6-di-t-butylphenol so that 10 to 30% by weight of t-butylphenols or total of t-butylphenols and phenol is present together with 100% by weight of 2,6-di-t-butylphenol.

The catalyst mixture obtained by dissolving the alkali metals employed as the catalyst, phenol and t-butylphenols are instantaneously soluble in arbitrary proportion in the purified 2,6-di-t-butylphenol, crude 2,6-di-t-butylphenol and the liquid after oxidative reaction thereof, so that homogeneous reaction condition can be obtained in any of a batch reaction and a continuous reaction.

That is, the desired oxidative reaction can be performed by charging the alkali metal catalyst, purified or crude 2,6-di-t-butylphenol and phenol or t-butylphenols into the reaction vessel, heating the mixture to a given temperature and blowing an oxygen containing gas such as air thereinto. While carrying out the oxidative reaction, the purified or crude 2,6-di-t-butylphenol and phenol or t-butylphenols can continuously be charged into the reaction mixture.

For example, 3,3',5,5'-tetra-t-butylbiphenol can be synthesized by adding phenol to purified 2,6-di-t-butylphenol in an amount of 10 to 30% by weight per 100% by weight of 2,6-di-t-butylphenol, adding a given amount of an alkali metal catalyst such as potassium hydroxide and blowing air thereinto at 180 to 230° C. to thereby effect an oxidation of 2,6-di-t-butylphenol.

Alternatively, the desired oxidative reaction can be performed by adding phenol together with the alkali metal catalyst to purified or crude 2,6-di-t-butylphenol, heating the mixture to a given temperature and blowing an oxygen containing gas such as air thereinto. While carrying out the oxidative reaction, the purified or crude 2,6-di-t-butylphenol, phenol and the alkali metal catalyst can continuously be charged into the reaction system.

Moreover, the desired oxidative reaction can be performed by separately adding the alkali metal catalyst and the t-butylphenols or liquid mixture of t-butylphenols and phenol to purified or crude 2,6-di-t-butylphenol, heating the mixture to a given temperature and blowing an oxygen containing gas such as air thereinto. While carrying out the oxidative reaction, the purified or crude 2,6-di-t-butylphenol, the t-butylphenols and the alkali metal catalyst, or the purified or crude 2,6-di-t-butylphenol, the t-butylphenols, the phenol and the alkali metal catalyst can separately be charged into the reaction system continuously.

The oxidative reaction temperature ranges from 150 to 250° C., preferably, from 180 to 200° C. Although the reaction pressure may be atmospheric or superatmospheric, the oxidative reaction is preferably conducted at superatmospheric pressure of 1 to 5 kg/cm².

Although the oxygen source for use in the oxidative reaction may be selected from among pure oxygen, air and an oxygen containing gas diluted with inert gas, the oxidative reaction is generally preferably conducted with the use of air or air diluted with nitrogen gas.

The amount of oxygen absorbed by the 2,6-di-t-butylphenol as a starting material of 3,3',5,5'-tetra-t-butylbiphenol ranges from 10 to 30 mol %, preferably, from 15 to 25 mol % per 100 mol % of charged 2,6-di-t-butylphenol.

When the oxygen absorption is low, 2,6-di-t-butylphenol remains unreacted in greater proportion to thereby lower the yield of 3,3',5,5'-tetra-t-butylbiphenol. On the other hand, when the oxygen absorption is too high, a large amount of by-products such as as 3,3',5,5'-tetra-t-butyldiphenoquinone (DPQ) occur.

In the production of 3,3',5,5'-tetra-t-butylbiphenol, which is an intermediate of 4,4'-biphenol, from 2,6-di-t-butylphenol as a starting material, the above second process for producing 3,3',5,5'-tetra-t-butylbiphenol according to the present invention enables obtaining 3,3',5,5'-tetra-t-butylbiphenol in high yield with the full utilization of 2,6-di-t-butylphenol charged in the reaction vessel without detriment to the selectivity of 3,3',5,5'-tetra-t-butylbiphenol.

EFFECT OF THE INVENTION

The first process for producing 3,3',5,5'-tetra-t-butylbiphenol according to the present invention enables homogeneously performing the oxidative coupling reaction through a homogeneous dispersion of the alkali metal catalyst in the starting material with the result that 3,3',5,5'-tetra-t-butylbiphenol can be obtained in high yield. Further, this process enables producing 3,3',5,5'-tetra-t-butylbiphenol both in batches and continuously.

In the production of 3,3',5,5'-tetra-t-butylbiphenol, which is an intermediate of 4,4'biphenol, from 2,6-di-t-butylphenol as a starting material, the second process for producing 3,3',5,5'-tetra-t-butylbiphenol according to the present invention enables obtaining 3,3',5,5'-tetra-t-butylbiphenol in high yield with the full utilization of 2,6-di-t-butylphenol charged in the reaction vessel without detriment to the selectivity of 3,3',5,5'-tetra-t-butylbiphenol. Although the average degree of oxidation of 2,6-di-t-butylphenol is in the range of about 70 to 80 mol % in the conventional process for producing 3,3',5,5'-tetra-t-butylbiphenol, the degree of oxidation of 2,6-di-t-butylphenol can be as high as, for example, 95 mol % in the second process for producing 3,3',5,5'-tetra-t-butylbiphenol according to the present invention.

4,4'-Biphenol of high purity, for example, 99.9% by weight or higher can be produced from the 3,3',5,5'-tetra-t-butylbiphenol obtained by the second process of the present invention by the conventional process for producing 4,4'-biphenol.

EXAMPLE

The present invention will now be illustrated in greater detail with reference to the following Examples, which in no way limit the scope of the invention.

Example 1

Phenol was reacted with isobutylene in the presence of an aluminum phenoxide catalyst by the customary procedure. Thereafter, the aluminum phenoxide catalyst was removed, thereby obtaining crude 2,6-di-t-butylphenol.

This crude 2,6-di-t-butylphenol contained, as by-products, 0.5% by weight of phenol, 4.8% by weight of o-t-butylphenol, 0.6% by weight of p-t-butylphenol, 1.3% by weight of 2,4-di-t-butylphenol and 15% by weight of 2,4,6-tri-t-butylphenol and contained, as a principal product, 77.3% by weight of 2,6-di-t-butylphenol.

600 g of the obtained crude 2,6-di-t-butylphenol was charged into a 1 lit. cylindrical glass flask having an inside diameter of 80 mm and a height of 180 mm, purged with nitrogen gas and heated to 195° C. to thereby obtain a liquid crude 2,6-di-t-butylphenol.

10 g of an alkali metal catalyst mixture obtained by adding 25 g of a 48% aqueous potassium hydroxide solution to a liquid mixture of 80 g of p-t-butylphenol (PTBP) and 10 g of phenol (PhOH) and conducting a mixing was dropped from the top of the cylindrical glass flask into the above obtained liquid crude 2,6-di-t-butylphenol. The alkali metal catalyst mixture was instantaneously dissolved in the liquid crude 2,6-di-t-butylphenol, thereby obtaining a homogeneous solution.

500 g of the resultant alkali metal catalyst containing crude 2,6-di-t-butylphenol was transferred to a 1 lit. autoclave, and an oxidative coupling was performed without agitation while blowing air thereinto at a rate of 150 ml/min for 6 hr under conditions such that the reaction temperature and reaction pressure were 195° C. and 3 kg/cm$^2$-G, respectively.

A gas chromatography analysis showed that the oxidative reaction mixture comprised 14.3% by weight of unreacted 2,6-di-t-butylphenol and 61.5% by weight of 3,3',5,5'-tetra-t-butylbiphenol. Further, it was shown that the degree of oxidation of 2,6-di-t-butylphenol was 81.8 mol % and that the existence yield of desired 3,3',5,5'-tetra-t-butylbiphenol was 79.4 mol % (based on charged 2,6-di-t-butylphenol).

Example 2

In place of the crude 2,6-di-t-butylphenol of Example 1, 600 g of purified 2,6-di-t-butylphenol having a purity of 99.9% was charged into a 1 lit. cylindrical glass flask having an inside diameter of 80 mm and a height of 180 mm, purged with nitrogen gas and heated to 195° C. to thereby obtain a liquid purified 2,6-di-t-butylphenol.

10 g of an alkali metal catalyst mixture obtained by adding 25 g of a 48% aqueous potassium hydroxide solution to a liquid mixture of 80 g of p-t-butylphenol (PTBP) and 10 g of phenol (PhOH) and conducting a mixing was dropped from the top of the cylindrical glass flask into the above obtained liquid purified 2,6-di-t-butylphenol. The alkali metal catalyst mixture was instantaneously dissolved in the liquid purified 2,6-di-t-butylphenol as observed in Example 1 thereby obtaining a homogeneous solution.

500 g of the resultant alkali metal catalyst containing purified 2,6-di-t-butylphenol was transferred to a 1 lit. autoclave, and an oxidative coupling was performed without agitation while blowing air thereinto at a rate of 150 ml/min for 8 hr under conditions such that the reaction temperature and reaction pressure were 195° C. and 3 kg/cm$^2$-G, respectively.

A gas chromatography analysis showed that the oxidative reaction mixture comprised 15.4% by weight of unreacted 2,6-di-t-butylphenol and 83.1% by weight of 3,3',5,5'-tetra-t-butylbiphenol. Further, it was shown that the degree of oxidation of 2,6-di-t-butylphenol was 84.6 mol % and that the existence yield of desired 3,3',5,5'-tetra-t-butylbiphenol was 83.6 mol % (based on charged 2,6-di-t-butylphenol).

Examples 3 and 4

600 g of crude 2,6-di-t-butylphenol of Example 1 was charged into a 1 lit. cylindrical glass flask having an inside diameter of 80 mm and a height of 180 mm, purged with nitrogen gas and heated to 195° C. to thereby obtain a liquid 2,6-di-t-butylphenol.

About 10 g of each of alkali metal catalyst mixtures consisting of a 48% aqueous potassium hydroxide solution, p-t-butylphenol (PTBP) and phenol (PhOH), specified in the following Table 1, was prepared and separately dropped from the top of the cylindrical glass flask into the above obtained liquid 2,6-di-t-butylphenol. The mode of dissolution of liquid drops was observed.

As a result, both the alkali metal catalyst mixtures specified in Table 1 were almost instantaneously dissolved in the liquid crude 2,6-di-t-butylphenol as observed in Example 1, thereby obtaining homogeneous solutions.

TABLE 1

| | | (alkali metal catalyst mixture) | | |
|---|---|---|---|---|
| Example No. | TBPs | TBPs/PhOH (wt. ratio) | TBPs/KOH (mol. ratio) | KOH conc. (wt. %) |
| 3 | PTBP | 80/20 | 2.5 | 9.6 |
| 4 | PTBP | 73/27 | 2.5 | 8.9 |

Note
TBPs: t-butylphenols, and
PTBP: p-t-butylphenol.

Examples 5 to 7

100 g of a liquid mixture of t-butylphenols and phenol was charged in a 500 ml four-necked flask. A given amount of a 48% aqueous potassium hydroxide solution was added thereto, heated to 200° C. and dehydrated. Thus, alkali metal catalyst mixtures (all solid at room temperature) specified in the following Table 2 were prepared.

600 g of crude 2,6-di-t-butylphenol having the same composition as in Example 1 was charged into the same cylindrical glass flask as in Example 1, purged with nitrogen gas and heated to 195° C. 5 to 10 g of each of the alkali metal catalyst mixtures (cakes) specified in Table 2 was separately dropped from the top of the flask thereinto. The mode of dissolution of the alkali metal catalyst mixture cakes was observed.

As a result, all the alkali metal catalyst mixture cakes specified in Table 2 were instantaneously dissolved in the liquid crude 2,6-di-t-butylphenol as observed in Example 1.

TABLE 2

| | | (alkali metal catalyst mixture) | | |
|---|---|---|---|---|
| Example No. | TBPs | TBPs/PhOH (wt. ratio) | TBPs/KOH (mol. ratio) | Water content (wt. %) |
| 5 | OTBP | 100/0 | 2.8 | 2.0 |
| 6 | PTBP | 90/10 | 2.3 | 2.0 |
| 7 | PTBP | 70/30 | 1.8 | 2.5 |

Note
TBPs: t-butylphenols,
OTBP: o-t-butylphenol, and
PTBP: p-t-butylphenol.

Comparative Example 1

600 g of crude 2,6-di-t-butylphenol having the same composition as in Example 1 was charged into a 1 lit. cylindrical glass flask having an inside diameter of 80 mm and a height of 180 mm, purged with nitrogen gas and heated to 195° C. to thereby obtain a liquid crude 2,6-di-t-butylphenol.

2.6 g of a 48% aqueous potassium hydroxide solution was dropped from the top of the cylindrical glass flask into the liquid crude 2,6-di-t-butylphenol. The aqueous potassium hydroxide solution settled in liquid drops on the bottom of the flask. Water was boiled off with the catalyst KOH left aggregating on the bottom of the flask.

500 g of the supernatant of the crude 2,6-di-t-butylphenol containing the alkali metal catalyst was transferred to a 1 lit. autoclave, and an oxidative coupling was performed without agitation while blowing air thereinto at a rate of 150 ml/min for 6 hr under conditions such that the reaction temperature and reaction pressure were 195° C. and 3 kg/cm²-G, respectively. The reaction rate was slow and the oxidative reaction stopped prior to completion of the reaction.

A gas chromatography analysis showed that the oxidative reaction mixture comprised 52.1% by weight of unreacted 2,6-di-t-butylphenol and 23.7% by weight of 3,3',5,5'-tetra-t-butylbiphenol. Further, it was shown that the degree of oxidation of 2,6-di-t-butylphenol was 33.0 mol % and that the existence yield of desired 3,3',5,5'-tetra-t-butylbiphenol was as low as 30.5 mol % (based on charged 2,6-di-t-butylphenol).

Comparative Examples 2 to 4

600 g of crude 2,6-di-t-butylphenol having the same composition as in Example 1 or 600 g of purified 2,6-di-t-butylphenol having a purity of 99.9% was charged into the same cylindrical glass flask as in Example 1, purged with nitrogen gas and heated to 195° C. 5 to 10 g of each of 48%, 24% and 6% aqueous potassium hydroxide solutions was separately dropped from the top of the flask thereinto. The mode of dissolution of liquid drops was observed.

As a result, in all the comparative examples specified in the following Table 3, each of the aqueous potassium hydroxide solutions settled in liquid drops on the bottom of the flask and, thereafter, water was boiled off with the catalyst KOH left aggregating on the bottom of the flask, as observed in Comparative Example 1.

TABLE 3

(aqueous alkali solution)

| Comp. Ex. No. | Starting mat'l 26B | Purity of 26B (wt. %) | Conc. of aq. KOH soln. (wt. %) |
|---|---|---|---|
| 2 | crude | 77.3 | 24 |
| 3 | crude | 77.3 | 6 |
| 4 | purified | 99.9 | 48 |

Note
26B: 2,6-di-t-butylphenol.

Comparative Examples 5 to 7

600 g of crude 2,6-di-t-butylphenol having the same composition as in Example 1 was charged into the same glass flask as in Examples 1 to 3, purged with nitrogen gas and heated to 195° C. to thereby obtain a liquid crude 2,6-di-t-butylphenol. 5 to 10 g of each of the alkali metal catalyst mixtures specified in the following Table 4 was separately dropped from the top of the flask thereinto. The mode of dissolution of liquid drops was observed.

As a result, in all the comparative examples specified in the following Table 4, each of the aqueous potassium hydroxide solutions settled in liquid drops on the bottom of the flask and, thereafter, water brought into contact with the flask bottom was boiled off with the catalyst KOH left aggregating on the bottom of the flask, as observed in Comparative Example 1.

TABLE 4

(alkali metal catalyst mixture)

| Comp. Ex. No. | TBPs | TBPs/PhOH (wt. ratio) | PhOH/KOH (mol. ratio) | Water Content (wt. %) | KOH conc. (wt. %) |
|---|---|---|---|---|---|
| 5 | PTBP | 67/33 | 1.5 | 11.2 | 10.4 |
| 6 | — | 0/100 | 2.5 | 2 | 21.4 |
| 7 | PTBP | 50/50 | 2.1 | 5 | 16 |

Note
TBPs: t-butylphenols, and
PTBP: p-t-butylphenol.

Example 8
(purified 2,6-di-t-butylphenol+phenol)

350 g of purified 2,6-di-t-butylphenol containing phenol as an impurity in an amount of not greater than 0.1% by weight was placed in a 1 lit. autoclave equipped with an agitator, a thermometer and a reflux condenser and, further, 35 g of phenol was added thereto so that the phenol content of purified 2,6-di-t-butylphenol was adjusted to 10% by weight based on the weight of 2,6-di-t-butylphenol.

1.0 g of a 48% aqueous potassium hydroxide solution as an alkali metal catalyst was added to the liquid mixture, and air was blown thereinto at a reaction temperature of 195° C. under a reaction pressure of 3 kg/cm²-G until the degree of oxidation of 2,6-di-t-butylphenol became 116 mol %. Thereafter, air blowing was stopped, and 75 g of purified 2,6-di-t-butylphenol was added to the reaction mixture, followed by agitation for about 1 hr and cooling. The thus obtained reaction mixture was analyzed by gas chromatography.

As a result, it was found that the reaction mixture comprised 4.5% by weight of unreacted 2,6-di-t-butylphenol, 0.3% by weight of tetra-t-butyldiphenoquinone and 85% by weight of 3,3',5,5'-tetra-t-butylbiphenol.

With respect to this reaction mixture, the degree of oxidation of charged 2,6-di-t-butylphenol was 95 mol % and the yield of 3,3',5,5'-tetra-t-butylbiphenol based on charged 2,6-di-t-butylphenol was 91 mol %.

150 g of p-t-butylphenol as a debutylation reaction solvent and 2.0 g of p-toluenesulfonic acid as a debutylation catalyst were added to 300 g of the thus obtained reaction mixture and heated at 180 to 220° C. to thereby carry out a debutylation reaction of 3,3',5,5'-tetra-t-butylbiphenol. Thereafter, the contents of 4,4'-biphenol and trihydroxybiphenyl in the reaction mixture were analyzed by liquid chromatography.

As a result, it was found that the proportion of trihydroxybiphenyl to 4,4'-biphenol was as low as 800 ppm.

Example 9
(purified 2,6-di-t-butylphenol+o-t-butylphenol)

350 g of purified 2,6-di-t-butylphenol containing o-t-butylphenol as an impurity in an amount of not greater than 0.1% by weight was placed in a 1 lit. autoclave equipped with an agitator, a thermometer and a reflux condenser and, further, 35 g of o-t-butylphenol was added thereto so that the o-t-butylphenol content of purified 2,6-di-t-butylphenol was adjusted to 10% by weight based on the weight of 2,6-di-t-butylphenol.

1.1 g of a 48% aqueous potassium hydroxide solution as an alkali metal catalyst was added to the liquid mixture, and air was blown thereinto at a reaction temperature of 195° C. under a reaction pressure of 3 kg/cm²-G until the degree of oxidation of 2,6-di-t-butylphenol became 120 mol %.

Thereafter, air blowing was stopped, and 97 g of purified 2,6-di-t-butylphenol was added to the reaction mixture, followed by agitation for about 1 hr and cooling. The thus obtained reaction mixture was analyzed by gas chromatography.

As a result, it was found that the reaction mixture comprised 4.5% by weight of unreacted 2,6-di-t-butylphenol, 0.1% by weight of tetra-t-butyldiphenoquinone and 84% by weight of 3,3',5,5'-tetra-t-butylbiphenol.

With respect to this reaction mixture, the degree of oxidation of charged 2,6-di-t-butylphenol was 95 mol % and the yield of 3,3',5,5'-tetra-t-butylbiphenol based on charged 2,6-di-t-butylphenol was 80 mol %.

150 g of p-t-butylphenol as a debutylation reaction solvent and 2.0 g of p-toluenesulfonic acid as a debutylation catalyst were added to 300 g of the thus obtained reaction mixture and heated at 180 to 220° C. to thereby carry out a debutylation reaction of 3,3',5,5'-tetra-t-butylbiphenol. Thereafter, the contents of 4,4'-biphenol and trihydroxybiphenyl in the reaction mixture were analyzed by liquid chromatography.

As a result, it was found that the proportion of trihydroxybiphenyl to 4,4'-biphenol was as low as 800 ppm.

Example 10
(crude 2,6-di-t-butylphenol+phenol)

350 g of crude 2,6-di-t-butylphenol containing phenol, o-t-butylphenol and 2,4,6-tri-t-butylphenol, as impurities, in respective amounts of 0.5% by weight, 5% by weight and 15% by weight and having a 2,6-di-t-butylphenol purity of 78% by weight was placed in a 1 lit. autoclave equipped with an agitator, a thermometer and a reflux condenser and, further, 17.5 g of phenol was added thereto so that the total content of phenol and o-t-butylphenol in crude 2,6-di-t-butylphenol was adjusted to 12.8% by weight based on the weight of 2,6-di-t-butylphenol.

1.0 g of a 48% aqueous potassium hydroxide solution as an alkali metal catalyst was added to the liquid mixture, and air was blown thereinto at a reaction temperature of 195° C. under a reaction pressure of 3 kg/cm$^2$-G until the degree of oxidation of 2,6-di-t-butylphenol became 120 mol %. Thereafter, air blowing was stopped, and 120 g of crude 2,6-di-t-butylphenol was added to the reaction mixture, followed by agitation for about 1 hr and cooling. The thus obtained reaction mixture was analyzed by gas chromatography.

As a result, it was found that the reaction mixture comprised 3.8% by weight of unreacted 2,6-di-t-butylphenol, 0.3% by weight of 3,3',5,5'-tetra-t-butyldiphenoquinone and 67.4% by weight of 3,3',5,5'-tetra-t-butylbiphenol. The yield of 3,3',5,5'-tetra-t-butylbiphenol based on charged 2,6-di-t-butylphenol was 90 mol %.

150 g of p-t-butylphenol as a debutylation reaction solvent and 2.0 g of p-toluenesulfonic acid as a debutylation catalyst were added to 300 g of the thus obtained reaction mixture and heated at 180 to 220° C. to thereby carry out a debutylation reaction of 3,3',5,5'-tetra-t-butylbiphenol. Thereafter, the contents of 4,4'-biphenol and trihydroxybiphenyl in the reaction mixture were analyzed by liquid chromatography.

As a result, it was found that the proportion of trihydroxybiphenyl to 4,4'-biphenol was as low as 600 ppm.

Example 11
(crude 2,6-di-t-butylphenol+phenol)

350 g of crude 2,6-di-t-butylphenol containing phenol, o-t-butylphenol and 2,4,6-tri-t-butylphenol, as impurities, in respective amounts of 0.5% by weight, 5% by weight and 15% by weight and having a 2,6-di-t-butylphenol purity of 78% by weight was placed in a 1 lit. autoclave equipped with an agitator, a thermometer and a reflux condenser and, further, 17.5 g of phenol was added thereto so that the total content of phenol and o-t-butylphenol in crude 2,6-di-t-butylphenol was adjusted to 12.8% by weight based on the weight of 2,6-di-t-butylphenol.

6 g of an alkali metal catalyst mixture obtained by adding 25 g of a 48% aqueous potassium hydroxide solution to a liquid mixture of 80 g of p-t-butylphenol (PTBP) and 10 g of phenol (PhOH) and conducting a mixing was dropped into the above obtained liquid. The alkali metal catalyst mixture was instantaneously dissolved in the above-obtained liquid crude 2,6-di-t-butylphenol, thereby obtaining a homogeneous solution.

Subsequently, air was blown thereinto at a reaction temperature of 195° C. under a reaction pressure of 3 kg/cm$^2$-G until the degree of oxidation of 2,6-di-t-butylphenol became 120 mol %. Thereafter, air blowing was stopped, and 120 g of crude 2,6-di-t-butylphenol was added to the reaction mixture, followed by agitation for about 1 hr and cooling. The thus obtained reaction mixture was analyzed by gas chromatography.

As a result, it was found that the reaction mixture comprised 3.8% by weight of unreacted 2,6-di-t-butylphenol, 0.3% by weight of tetra-t-butyldiphenoquinone and 67.4% by weight of 3,3',5,5'-tetra-t-butylbiphenol. The yield of 3,3',5,5'-tetra-t-butylbiphenol based on charged 2,6-di-t-butylphenol was 90 mol %.

150 g of p-t-butylphenol as a debutylation reaction solvent and 2.0 g of p-toluenesulfonic acid as a debutylation catalyst were added to 300 g of the thus obtained reaction mixture and heated at 180 to 220° C. to thereby carry out a debutylation reaction of 3,3',5,5'-tetra-t-butylbiphenol. Thereafter, the contents of 4,4'-biphenol and trihydroxybiphenyl in the reaction mixture were analyzed by liquid chromatography.

As a result, it was found that the proportion of trihydroxybiphenyl to 4,4'-biphenol was as low as 600 ppm.

Comparative Example 8
(purified 2,6-di-t-butylphenol only)

350 g of purified 2,6-di-t-butylphenol containing phenol as an impurity in an amount of not greater than 0.1% by weight was placed in a 1 lit. autoclave equipped with an agitator, a thermometer and a reflux condenser. 1.0 g of a 48% aqueous potassium hydroxide solution as an alkali metal catalyst was added thereto, and air was blown thereinto at a reaction temperature of 195° C. under a reaction pressure of 3 kg/cm$^2$-G until the degree of oxidation of 2,6-di-t-butylphenol became 120 mol %. Thereafter, air blowing was stopped, and 110 g of purified 2,6-di-t-butylphenol was added to the reaction mixture, followed by agitation for about 1 hr and cooling. The thus obtained reaction mixture was analyzed by gas chromatography.

As a result, it was found that the reaction mixture comprised 5% by weight of unreacted 2,6-di-t-butylphenol, 1% by weight of tetra-t-butyldiphenoquinone and 92% by weight of 3,3',5,5'-tetra-t-butylbiphenol.

With respect to this reaction mixture, the degree of oxidation of charged 2,6-di-t-butylphenol was 95 mol % and the yield of 3,3',5,5'-tetra-t-butylbiphenol based on charged 2,6-di-t-butylphenol was 85 mol %.

150 g of p-t-butylphenol as a debutylation reaction solvent and 2.0 g of p-toluenesulfonic acid as a debutylation catalyst were added to 300 g of the thus obtained reaction mixture and heated at 180 to 220° C. to thereby carry out a debutylation reaction of 3,3',5,5'-tetra-t-butylbiphenol.

Thereafter, the contents of 4,4'-biphenol and trihydroxybiphenyl in the reaction mixture were analyzed by liquid chromatography.

As a result, it was found that the proportion of trihydroxybiphenyl to 4,4'-biphenol was as high as 3600 ppm.

Comparative Example 9
(crude 2,6-di-t-butylphenol only)

350 g of crude 2,6-di-t-butylphenol containing phenol, o-t-butylphenol and 2,4,6-tri-t-butylphenol, as impurities, in respective amounts of 0.5% by weight, 5% by weight and 15% by weight and having a 2,6-di-t-butylphenol purity of 78% by weight was placed in a 1 lit. autoclave equipped with an agitator, a thermometer and a reflux condenser. 1.0 g of a 48% aqueous potassium hydroxide solution as an alkali metal catalyst was added thereto, and air was blown thereinto at a reaction temperature of 195° C. under a reaction pressure of 3 kg/cm$^2$-G until the degree of oxidation of 2,6-di-t-butylphenol became 123 mol %. Thereafter, air blowing was stopped, and 120 g of crude 2,6-di-t-butylphenol was added to the reaction mixture, followed by agitation for about 1 hr and cooling. The thus obtained reaction mixture was analyzed by gas chromatography.

As a result, it was found that the reaction mixture comprised 4% by weight of unreacted 2,6-di-t-butylphenol, 1.2% by weight of tetra-t-butyldiphenoquinone and 69% by weight of 3,3',5,5'-tetra-t-butylbiphenol. The yield of 3,3',5,5'-tetra-t-butylbiphenol based on charged 2,6-di-t-butylphenol was 86 mol %.

150 g of p-t-butylphenol as a debutylation reaction solvent and 2.0 g of p-toluenesulfonic acid as a debutylation catalyst were added to 300 g of the thus obtained reaction mixture and heated at 180 to 220° C. to thereby carry out a debutylation reaction of 3,3',5,5'-tetra-t-butylbiphenol. Thereafter, the contents of 4,4'-biphenol and trihydroxybiphenyl in the reaction mixture were analyzed by liquid chromatography.

As a result, it was found that the proportion of trihydroxybiphenyl to 4,4'-biphenol was as high as 4000 ppm.

What is claimed is:

1. A process for producing 3,3',5,5'-tetra-t-butylbiphenol, comprising conducting an oxidative dimerization of purified 2,6-di-t-butylphenol (i) or crude 2,6-di-t-butylphenol (ii), said crude 2,6-di-t-butylphenol being obtained by reacting isobutylene with phenol in the presence of an aluminum catalyst, and removing the aluminum catalyst, wherein the oxidative dimerization of (i) or (ii) is performed in the presence of an alkali metal catalyst mixture to thereby obtain 3,3',5,5'-tetra-t-butylbiphenol, wherein said catalyst mixture comprises:
   (1) alkali metal catalyst and alkylphenols, or
   (2) alkali metal catalyst, alkylphenols and phenol.

2. The process as claimed in claim 1, wherein the alkylphenols are contained in the catalyst mixture (1) or catalyst mixture (2) in an amount of 1 to 5 times mole of the alkali metal catalyst, and water is contained in the catalyst mixture (1) or catalyst mixture (2) in an amount of 2 to 20% by weight.

3. The process as claimed in claim 2, wherein the catalyst mixture (2) contains alkylphenols and phenol in a weight ratio of alkylphenols/phenol of at least 70/30.

4. The process as claimed in any of claims 1 to 3, wherein the alkylphenols consist of p-t-butylphenol.

5. A process for producing 3,3',5,5'-tetra-t-butylbiphenol, comprising conducting an oxidative coupling of purified 2,6-di-t-butylphenol (i) or crude 2,6-di-t-butylphenol (ii), said crude 2,6-di-t-butylphenol being obtained by reacting isobutylene with phenol in the presence of an aluminum catalyst, and removing the aluminum catalyst, wherein the oxidative coupling of (i) or (ii) is performed in the presence of an alkali metal catalyst to thereby obtain 3,3',5,5'-tetra-t-butylbiphenol, wherein the oxidative coupling is conducted in the presence of 10 to 30% by weight of phenol and/or t-butylphenols per 100% by weight of 2,6-di-t-butylphenol.

6. The process as claimed in claim 5, wherein the t-butylphenols consist of o-t-butylphenol.

7. The process as claimed in claim 5, wherein the crude 2,6-di-t-butylphenol (ii) is obtained by reacting isobutylene with phenol in the presence of an aluminum phenoxide catalyst and the crude 2,6-di-t-butylphenol contains phenol in an amount of not greater than 1.0% by weight, o-t-butylphenol in an amount of not greater than 5% by weight and t-butylphenols other than o-t-butylphenol and 2,4,6-tri-t-butylphenol in an amount not greater than 3% by weight.

8. The process as claimed in any of claims 5 to 7, wherein phenol together with an alkali metal catalyst is added to purified 2,6-di-t-butylphenol or crude 2,6-di-t-butylphenol, or phenol is directly added to purified 2,6-di-t-butylphenol or crude 2,6-di-t-butylphenol so that 10 to 30% by weight of phenol or 10 to 30% by weight of a total of phenol and o-t-butylphenol is present together with 100% by weight of 2,6-di-t-butylphenol.

9. The process as claimed in any of claims 5 to 7, wherein t-butylphenols or t-butylphenols together with phenol are directly added to purified 2,6-di-t-butylphenol or crude 2,6-di-t-butylphenol so that 10 to 30% by weight of t-butylphenols or 10 to 30% by weight of a total of t-butylphenols and phenol are present together with 100% by weight of 2,6-di-t-butylphenol.

10. The process as claimed in claim 1, wherein the alkali metal catalyst is used in an amount ranging from about 0.3 to 1.5 mol % per 100 mol % of 2,6-di-t-butylphenol.

11. The process as claimed in claim 1, wherein the alkylphenols are at least one selected from the group consisting of o-t-butylphenol, p-t-butylphenol, m-t-butylphenol, 2,4-di-t-butylphenol and mixtures thereof.

12. The process as claimed in claim 1, wherein reaction temperature ranges from about 150 to 250° C.

13. The process as claimed in claim 1, wherein reaction pressure ranges from about 1 to 5 kg/cm$^2$.

14. The process as claimed in claim 5, wherein the alkali metal catalyst is used in an amount ranging from about 0.3 to 1.5 mol % per 100 mol % of 2,6-di-t-butylphenol.

15. The process as claimed in claim 5, wherein reaction temperature ranges from about 150 to 250° C.

16. The process as claimed in claim 1, wherein reaction pressure ranges from about 1 to 5 kg/cm$^2$.

* * * * *